(12) United States Patent
Carver

(10) Patent No.: US 7,366,365 B2
(45) Date of Patent: Apr. 29, 2008

(54) TISSUE SCANNING APPARATUS AND METHOD

(75) Inventor: Gary Carver, Flemington, NJ (US)

(73) Assignee: Princeton Lightwave, Inc., Cranbury, NJ (US)

( * ) Notice: Subject to any disclaimer, the term of this patent is extended or adjusted under 35 U.S.C. 154(b) by 9 days.

(21) Appl. No.: 11/602,724

(22) Filed: Nov. 21, 2006

(65) Prior Publication Data

US 2007/0167839 A1   Jul. 19, 2007

Related U.S. Application Data

(60) Provisional application No. 60/739,863, filed on Nov. 23, 2005.

(51) Int. Cl.
    G02B 6/00    (2006.01)
    G02B 26/08   (2006.01)
    G01J 3/28    (2006.01)

(52) U.S. Cl. .............. 385/12; 600/473; 600/476; 600/478; 356/326; 356/328; 359/202

(58) Field of Classification Search ............ 385/12
    See application file for complete search history.

(56) References Cited

U.S. PATENT DOCUMENTS

| 5,155,785 | A | 10/1992 | Holland et al. |
| 5,259,051 | A | 11/1993 | Burack et al. |
| 5,309,534 | A | 5/1994 | Cohen et al. |
| 5,421,930 | A | 6/1995 | Holland |
| 5,461,475 | A | 10/1995 | Lerner et al. |
| 5,680,490 | A | 10/1997 | Cohen et al. |
| 5,737,121 | A * | 4/1998 | Dixon .................. 359/388 |
| 6,091,525 | A | 7/2000 | Cundiff |
| 6,370,422 | B1 * | 4/2002 | Richards-Kortum et al. ..... 600/478 |
| 6,452,681 | B1 * | 9/2002 | Carver et al. ............... 356/450 |
| 6,470,124 | B1 * | 10/2002 | Le Gargasson et al. .... 385/117 |
| 6,687,000 | B1 * | 2/2004 | White .................... 356/328 |
| 6,747,795 | B2 * | 6/2004 | Lin et al. ................. 359/385 |
| 2004/0109164 | A1 * | 6/2004 | Horii et al. .............. 356/479 |
| 2005/0035295 | A1 * | 2/2005 | Bouma et al. ........... 250/341.1 |
| 2005/0238070 | A1 * | 10/2005 | Imeshev et al. ............ 372/21 |
| 2006/0217594 | A1 * | 9/2006 | Ferguson ................ 600/175 |

OTHER PUBLICATIONS

Urey, "Resonant MOEMS scanner design and dynamics", Aug. 20-23, 2002, IEEE, pp. 83-84.*

* cited by examiner

Primary Examiner—Hemang Sanghavi
Assistant Examiner—Kaili Prince
(74) Attorney, Agent, or Firm—Howard IP Law Group

(57) ABSTRACT

A system for multispectral confocal mapping of a tissue, comprising: a light source; an optical fiber having an aperture providing a confocal pinhole, a scanner being free-space coupled to said aperture and operative to scan the tissue and provide intensity signals for each of a plurality of points therein; a switch or modulator operative to convert input signals to optical pulses; a reflector that receives the optical pulses and provides a temporal sequence of wavelength selective reflections; and, a detector optically coupled to receive the temporal sequence of wavelength selective reflections.

32 Claims, 7 Drawing Sheets

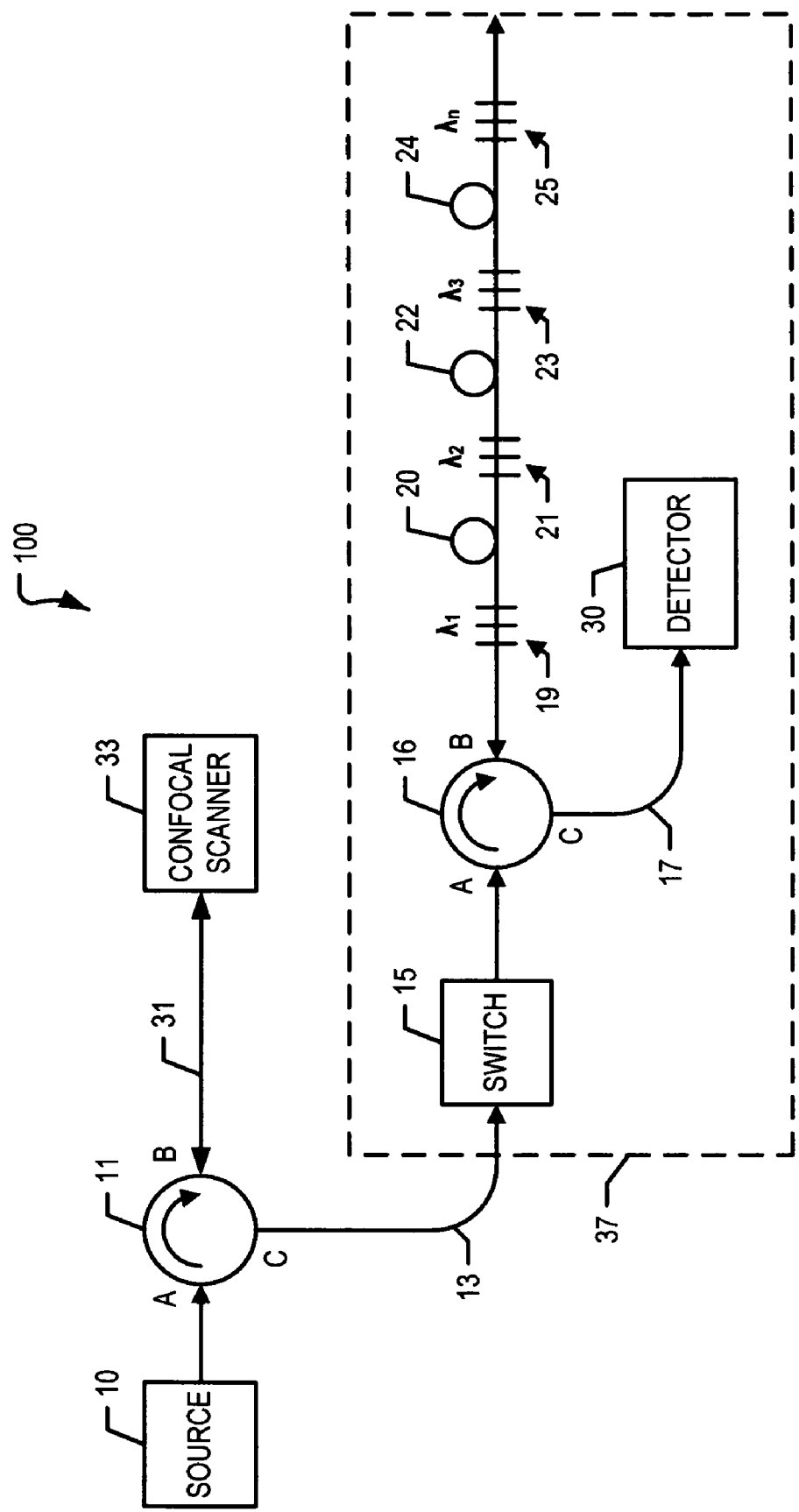

TISSUE SCANNING APPARATUS AND METHOD

RELATED APPLICATION

This application claims the benefit of U.S. Provisional Patent Application No. 60/739,863, filed Nov. 23, 2005, entitled "Fast Spectrometer Apparatus" which application is incorporated herein by reference in its entirety.

FIELD OF THE INVENTION

The present invention relates generally to imaging systems, and more particularly to a high speed spectrometer for multispectral confocal mapping.

BACKGROUND OF THE INVENTION

Various imaging systems and techniques have been used for biomedical applications, such as tissue mapping. One approach to tissue mapping involves multispectral imaging, where the tissue to be mapped is conjugate with a detector array. The array may be a charge coupled device (CCD) or a photo-diode array. In the array, the spatial data is directly obtained in the image. A tunable filter can be placed before the detector array, and images collected for each color setting of the filter. Liquid crystal tunable filters (LCTF) and acousto-optic tunable filters (AOTF) have been used and are available for such systems. See, for example, "*Development of a Multi-Spectral Imaging System for Optical Diagnosis of Malignant Tissues*" by Noordmans et al, Photonics West, 2005. See, also, "*AOTF Microscope for Imaging with Increased Speed and Spectral Versatility*", by D. L. Farkas et al, published in *Biophysical Journal*, Volume 73, 1997.

As an alternative to a tunable filter, a volume hologram can be placed before the detector array, with images collected by pixel arrays positioned where each color is diffracted. See "*Computed Tomography Based Spectral Imaging for Fluorescence Microscopy*", by M. R. Descour, *Biophysical Journal*, Volume 80, 2001.

However, each of these methods is limited in terms of temporal response time. The LCTF tuning method requires about 100 milliseconds per wavelength, which corresponds to about three 3 seconds per spectrum of 30 colors. The AOTF tuning method requires about 25 microseconds per wavelength, or 0.75 ms per spectrum of 30 colors. Both filters face CCD read-out times of at least 3 milliseconds per image or 90 milliseconds per datacube (i.e. x by y by wavelength arrays of data) containing 30 images. Integration times often necessitate much longer acquisition times, often as long as several seconds, which are too long for live biological samples that move on shorter time scales. The volume holographic method has no tuning time requirement, but is also limited by the CCD read-out rates and integration times. The AOTF imaging method represents the state of art in this field but faces limited throughput and spatial misregistrations of one color with respect to another. Examples include U.S. Pat. No. 5,216,484, entitled "Real Time Imaging Spectrometer" and U.S. Pat. No. 5,796,512, entitled "Sub-Micron Imaging System Having an Acousto-Optical Tunable Filter".

Another approach uses confocal microscopy. Confocal microscopy is a technique that creates high resolution images of a variety of objects. Confocal microscopy differs from conventional optical microscopy in that it uses a condenser lens to focus illuminating light from a point source into a very small, diffraction limited spot within a specimen, and an objective lens to focus the light emitted from that spot onto a small pinhole in an opaque screen. A detector which is capable of quantifying how much light passes through the pinhole at any instant is located behind the screen. Because only light from within the illuminated spot is properly focused to pass through the pinhole and reach the detector, any stray light from structures above, below, or to the side of the illuminated spot are filtered out. The image quality is therefore greatly enhanced as compared to other approaches.

A coherent image is built up by scanning point by point over the desired field of view and recording the intensity of the light emitted from each spot, as small spots are illuminated at any one time. Scanning can be accomplished in several ways, including for example, via laser scanning.

A particular field of study, known as multi-spectral confocal mapping, holds great promise for imaging cancer cells at the cellular and molecular levels. See "*In-Vivo Cytometry: A Spectrum of Possibilities*," by D. L. Farkas et al, *Cytometry*, 2005. The National Institute of Health (NIH) has also encouraged research and development pertaining to in-vivo image guided cancer interventions. Biomedical researchers are working to detect tumor angiogenesis (via specific proteins and gene patterns), perform optical biopsies, perform treatments (optical surgery or photodynamic therapy), and monitor long term results. These goals require high spatial, spectral, and temporal resolution. Confocal microscopy can map millimeter sized fields of view with micron spatial resolution. Spectroscopic tools can provide multi-spectral data during laser excitation of fluorescence, 2-photon, and Raman spectroscopies. This is especially important when samples are labeled with a variety of molecular-specific contrast agents. See "*Optical Molecular Imaging for Early Detection of Cancer*," by R. Richards-Kortum et al, *OSA Topical Meeting on Biomedical Optics*, April, 2004. Other applications include neural imaging, intra-cellular proteomics, micro-vascular testing, plaque detection, foodstuff testing, and the evaluation of pharmaceutical products. Further, these spatial and spectral measurements should allow for the detection of sub-millisecond dynamics in living systems. However, the above-described features and characteristics are not available in one cost-effective instrument.

Confocal microscopes are commercially available through entities such as Carl Zeiss, Nikon, and Olympus. Confocal endoscopes have also been employed in the medical field for endoscopic operations. Some of these endoscopes are quite advanced and reference is made to U.S. Pat. No. 6,522,444 entitled "Integrated Angled-Dual-Axis Confocal Scanning Endoscopes" by Michael J. Mandella, et al., dated Feb. 18, 2003 and assigned to Optical Biopsy Technologies Inc., for example. In this patent, there is described an integrated angled dual access confocal scanning endoscope which uses silicon micro-machined mirrors and fiber coupled instruments to enable better resolution and faster scanning. It employs one of two illumination beams in an angled dual access scanning endoscope which provides an assortment of reflected and fluorescent images. Endoscopes used for biological and medical imaging applications are further described in "MEMS Optical Scanners for Microscopes", Miyajima et al, IEEE Journal of Selected Topics in Quantum Electronics, Volume 10, May/June 2004. In the described instruments, only one or a small number of wavelengths can be measured during each spatial scan. A high resolution fast multi-spectral confocal mapping technique and apparatus is desired.

SUMMARY OF THE INVENTION

In one aspect of the present invention, a system for multispectral confocal mapping of a tissue, includes: a light source providing emissions; an optical fiber having a first end optically coupled to receive the emissions and a second end having an aperture providing a confocal pinhole, a scanner being free-space coupled to the aperture, the scanner operative to scan the tissue and provide intensity signals for each of a plurality of points therein, wherein the optical fiber receives the intensity signals at the aperture and propagates the intensity signals to the first end; a switch or modulator optically coupled to the first end of the optical fiber and operative to convert the intensity signals to optical pulses; a reflector optically coupled to receive the optical pulses and provide a temporal sequence of wavelength selective reflections of the optical pulses; and, a detector optically coupled to receive the temporal sequence of wavelength selective reflections and provide an output suitable for populating a data cube indicative of the relative intensity of each point in the scanned tissue.

In another aspect, a system for multispectral confocal mapping of a tissue, includes: a light source providing a series of broad spectrum emission pulses; a plurality of reflectors optically coupled to receive the series of optical pulses and provide a temporal sequence of wavelength selective reflections of each of the optical pulses; an optical fiber having a first end optically coupled to receive the temporal sequence of wavelength selective reflections and a second end having an aperture providing a confocal pinhole, a scanner being free-space coupled to the aperture, the scanner operative to scan the tissue and provide intensity signals for each of a plurality of points therein, wherein the optical fiber receives the intensity signals at the aperture and propagates the intensity signals to the first end; and, a detector optically coupled to receive the intensity signals and provide an output suitable for populating a data cube indicative of the relative intensity of each point in the tissue scanned.

In still another aspect a method for mapping a tissue includes: scanning a plurality of portions of the tissue, and for each portion: coupling intensity signals from the then scanned portion of the tissue into an end of an optical fiber providing a confocal pinhole, converting the intensity signals to optical pulses; providing a temporal sequence of wavelength selective reflections of the optical pulses; and, providing an output indicative of a relative intensity in response to the temporal sequence of wavelength selective reflections.

In yet another aspect, a method includes: providing a temporal series of optical pulses; providing a temporal sequence of wavelength selective reflections of each of the optical pulses; impinging portions of the tissue with a corresponding one of the temporal sequence of wavelength selective reflections; detecting light returned from each portion in response to the impinging step; and providing an output indicative of a relative intensity for each portion of the tissue in response to the detecting.

BRIEF DESCRIPTION OF THE DRAWING

Understanding of the present invention will be facilitated by consideration of the following detailed description of the preferred embodiments of the present invention taken in conjunction with the accompanying drawings, in which like numerals refer to like parts and in which:

FIG. 1 depicts a fast grating spectrometer utilized with a confocal scanner to scan tissues, according to an embodiment of the invention.

DETAILED DESCRIPTION OF PREFERRED EMBODIMENTS OF THE INVENTION

Figure 2A:
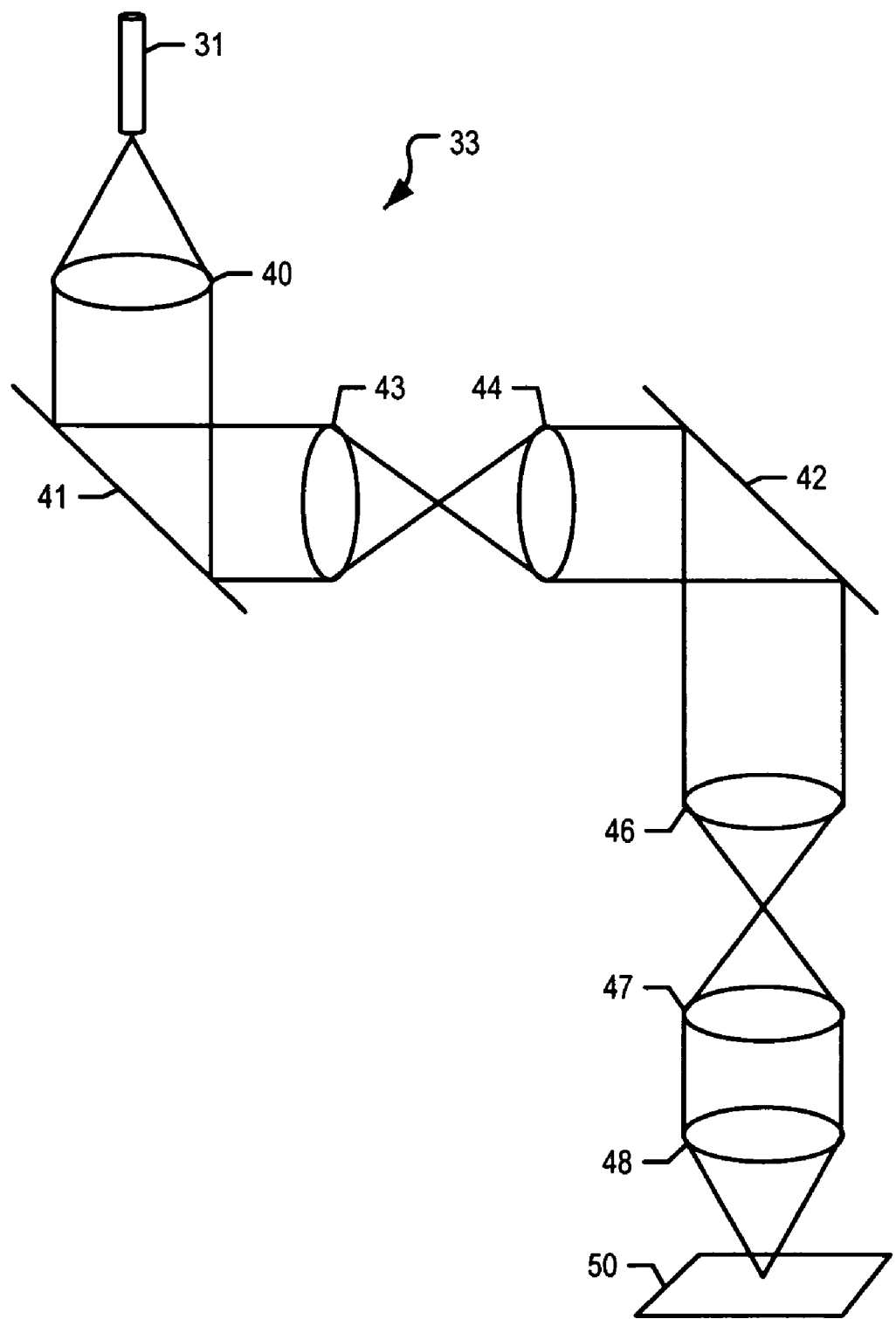
FIG. 2A depicts a scanner configuration suitable for use with ex-vivo tissues.

It is to be understood that the figures and descriptions of the present invention have been simplified to illustrate elements that are relevant for a clear understanding of the present invention, while eliminating, for purposes of clarity, many other elements found in typical optical methods and systems. However, because such elements are well known in the art, and because they do not facilitate a better understanding of the present invention, a discussion of such elements is not provided herein. The disclosure herein is directed to all such variations and modifications known to those skilled in the art.

In general, a confocal spatial scan is employed in conjunction with a fast fiber grating spectrometer. The combination maps wavelengths into time slots and is fiber based. The fiber that connects the fast optical spectrum analyzer to the scanner functions as a pinhole in a confocal microscope. In this manner, the cleaved end-face of a fiber provides the confocal pinhole. The spectrum analyzer enables one to provide spectra derived by unblazed fiber gratings having delay lines between the gratings and using a single element detector. In this manner, data cubes can be provided for multiple X-Y points in a tissue sample in a fast and efficient manner using a confocal microscope.

Referring to FIG. 1 there is shown a diagram depicting a confocal scanning system 100 according to an embodiment of the invention. System 100 is suitable for scanning in-vivo or ex-vivo tissues, as will be described. System 100 broadly encompasses the concept that spectra can be acquired for each pixel in a confocal spatial scan using a fast fiber grating spectrometer.

System 100 includes a radiation source 10. Source 10 provides radiation of one or more wavelengths either in a continuous (CW) and/or pulsed mode of operation. The radiation may be of any wavelength, or group or range of wavelengths useful in tissue scanning. Source 10 may take the form of a module that includes one or more laser sources. Source 10 may provide emissions in the form of a substantially single frequency laser line (for inducing fluorescence or Raman scattering) or a spectrally broad source (for reflectance studies), by way of example. In the case of spectrally broad emissions, source 10 may incorporate a collection of lasers, one or more superluminescent diodes (SLDs), one or more amplified spontaneous emission (ASE) sources, and/or a super-continuum source, for example.

In general, with regard to the embodiment illustrated in FIG. 1, a narrow band signal source such as a single laser output is provided directly to a sample of tissue (not shown) via confocal scanner 33 through circulator 11 and induces fluorescence in the sample. The fluorescence is a spectrally broad signal generated by the sample based on the excitation from the narrow band laser. The spectrally broad light from the tissue sample is returned through the confocal scanner and input to the spectrometer 37, which separates out the different colors of the fluorescence. In this manner, a monochromatic laser input on the sample generates a spectrally broad beam which is analyzed by the spectrometer.

More particularly, with regard to FIG. 1, emissions emanating from source 10 are applied to a first port A of a circulator 11, such as via optical fiber. Optical fibers employed are preferably single mode fibers (SMF); but other fibers such as multi-mode fibers (MMF), microstructured fibers (MSF), and polarization maintaining fibers (PMF) may be used. For non-limiting purposes of explanation, a multi-mode fiber has a thicker core than a single mode fiber, such that a MMF can collect more light (but may allow for reduced spectral resolution). Single mode fibers are well known and may have core diameters between about one to three micrometers (microns) for operation in the visible region (400 to 800 nanometers (nm)), and core diameters between about 8 to 10 microns for operation in the near infrared region (1100 to 1600 nm). It is understood, however, that other diameter fibers may also be used. Microstructured fibers can offer a single mode fiber with large core size and large numerical aperture for higher optical collection efficiency with high spectral resolution. Polarization maintaining fibers can preserve the polarization state of the signals (and may serve to improve system efficiency when replacing one or more circulators with polarization dependent coupler(s)).

Circulator 11 has additional ports B, C. Circulator 11 operates in a conventional manner to provide sequential outputs, e.g., to couple port A to port B, port B to port C. Port B of circulator 11 is coupled via optical fiber 31 to confocal scanner 33. Port C of circulator 11 is coupled via optical fiber 13 to a wavelength slicer and detector 37. Other coupling components, such as 3 dB couplers, may be used in addition or in lieu of circulators to provide the illustrated connectivity.

Optical fiber 13 couples port C of circulator 11 to an input of a switch 15. Switch 15 may take the form of an optical switch and convert emissions received into a pulse of a given temporal period (i.e., pulse width) at an output thereof. Switching operations in the optical field are well known. One can utilize electro-optic devices (e.g., lithium niobate), magneto-optic switches, or fast mechanical shutters, for example. While the embodiment of FIG. 1 illustrates switch 15 as part of spectrometer 37 in an exemplary configuration, other configurations are contemplated. For example, it is understood that switch 15 can alternatively be disposed between source 10 and circulator 11.

In the embodiment of FIG. 1, switch 15 has an output coupled to a port A of a second circulator 16. Port B of circulator 16 is directed through an optical fiber to a series coupled plurality of fiber gratings 19, 21, 23, 25 (four of which are shown). In one embodiment of the present invention, the gratings are unblazed and have matching frequencies corresponding to wavelengths designated as $\lambda_1$, $\lambda_2$, $\lambda_3$ and $\lambda_n$, respectively. Each grating may enable frequency selection at its corresponding matching frequency. By way of further, non-limiting example, each grating is responsive to a different wavelength or frequency, designated herein as the matching frequencies. Optical path delays 20, 22, 24 (three of which are shown) may be provided between gratings. In one embodiment of the present invention, each delay may take the form of a length, or loop, of optical fiber in the fiber, which causes pulses traversing it to propagate along the length or loop, and dependent thereupon introduces a corresponding delay. While four gratings and three delays are shown, the array may consist numerous such gratings (for example, 30 or 40 gratings) each associated with its own delay loop.

Referring still to FIG. 1, the gratings 19, 21, 23, 25 and delay elements 20, 22, 24, form a serially coupled fiber grating and delay array that provides a temporal sequence of wavelength selective reflections of broad spectrum optical pulses input thereto. Light returned by confocal scanner 33 is provided at port A and B of circulator 16, and propagates into the fiber grating and delay array. Light of wavelength $\lambda_1$ is reflected by grating 19. Light of wavelength $\lambda_2$ is reflected by grating 21. Light of wavelength $\lambda_3$ is reflected by grating 23, and so on, until light of wavelength $\lambda_n$ is reflected by grating 25. Light reflected by grating 19 (of wavelength $\lambda_1$) is the first to arrive at detector 30, as it enters circulator 16 and is directed through the fiber 17 into detector 30. The remainder of light reflected by the gratings 21, 23, 25 is delayed by the delay lengths or loops 20, 22, 24, such that the next light that arrives at the detector is of wavelength $\lambda_2$, and so on. The operation of wavelength slicer and detector such as 37 is more fully described in conjunction with wave division multiplexing applications in U.S. Pat. No. 6,452,681, entitled OPTICAL SPECTRUM ANALYZER, the entire disclosure of which is hereby incorporated by reference herein.

Such an array may be introduced into an optical fiber in any conventional manner. For example, direct write, phase mask, or other suitable methods may be utilized to selectively write the gratings on the fiber, as is understood by those skilled in the art. Other grating and delay configurations may also be used though. For example, one or more gratings that are chirped (e.g. via strain) or by using the electro-optic effect may be used in addition or in lieu of the illustrated grating array.

Referring still to FIG. 1, port C of circulator 16 is coupled via optical fiber 17 to an input of a detector 30. Detector 30 may take the form of a single element device and/or be of several types. A high gain low noise detector, such as a photomultiplier tube (PMT), may be well suited for use with low light level (<1 nW) visible wavelength applications. Photodiodes may be well suited for use with higher signal (>1 nW) and near infrared applications. Photo diode detectors are well known and fall into two general categories, namely, depletion layer type and avalanche type (often called an avalanche photodiode (APD)). The difference between such detectors is the existence of a gain mechanism. Depletion layer photo diodes include the PN junction diode, the PIN diode, the Schottky barrier diode, the point contact diode and the hetero junction diode, for example.

Referring still to FIG. 1 and as set forth above, port B of circulator 11 is coupled via optical fiber 31 to confocal scanner 33. According to an embodiment of the present invention, an end-face, or terminice, of optical fiber 31 proximate confocal scanner 33 is cleaved, such that the optical fiber 31 aperture serves as a confocal pinhole. According to an embodiment of the present invention, confocal scanner 33 is a free-space coupled device, such that this cleaved end-face, or terminice, connects the optical fiber coupled path to the scanner 33 free space optical path. The spectra of either an in- or ex-vivo tissue sample can be acquired for each pixel in the confocal spatial scan depending upon the nature of scanner 33 by using the fast fiber grating spectrometer 37.

As indicated, optical fiber 31 that connects circulator 11 to scanner 33 acts as the pinhole in a confocal microscope.

Thus this device uses fast spectroscopy with fast spatial scanning to create data cubes at the output of detector 30. For non-limiting purposes of further explanation, a data cube includes a plurality of images in the X-Y directions. Each image is two dimensional and provides information (for a given wavelength) regarding the sample at each scanning point. Thus one can obtain datacubes in real-time, whereby a fully populated data cube may be formed in several milliseconds, by way of further non-limiting example only. In such a mode of operation, the optical signals should be shot limited, meaning that the signal-to-noise ratio (S/N) is given by:

$$S/N = I_k/(2eB \cdot 1.2 \cdot (I^k + 2I_d))^{1/2}$$

where B is bandwidth, $I_k$ is signal current, and $I_d$ is dark current. When a signal is shot limited, the S/N is driven by signal strength. In this case, signal strength is a function of fluorescent yield, optical collection efficiency, and spectrometer throughput. An accepted figure of merit (FOM) states that each acquired data point be equivalent to at least 100 photons (for visible photons this is equates to 200 pW and an S/N equal to about 3.7).

In very low light level applications (e.g., picowatts (pW)), detector 30 may take the form of a single photon counting detector (e.g., a photon counting PMT or an APD operating in Geiger mode). A geiger mode APD generates a large surge of electrons for a single incident photon. This surge can be considered as a single count of a digital signal (e.g., it is either "on" or "off"). If multiple scans are performed on the same x-y area while adding the number of "single photon counts" for each resolved spot, one can use the number of counts to compute a grey level for each resolved spot. This applies single photon counting technology to multi-spectral confocal scanning.

Referring again to operation of the embodiment of FIG. 1, emission pulsing by switch 15 and/or source 10 modulation may be synchronized with pixel selection in the confocal scan. The emission pulses may be synchronized with X and Y deflectors depicted in FIGS. 2A and 2B.

Referring now also to FIG. 2A, there is shown a schematic representation of a confocal scanner well suited for scanning ex-vivo tissue samples 50 (one of which is shown), according to an embodiment of the present invention. An end of the fiber 31 is free-space, optically coupled with a collimating lens 40. Collimated emissions from source 10 impinge upon a first deflector 41. In the illustrated embodiment, deflector 41 provides for selective beam-steering in an X-direction. The deflector 41 may be a resonant scanner or a galvanometer, as are well known. Deflector 41 deflected emissions are directed to a second deflector 42, via lenses 43, 44. In the illustrated embodiment, deflector 42 provides for selective beam-steering in an Y-direction. The deflector 42 may be a resonant scanner or a galvanometer, as are well known.

Deflectors 41 and 42 may take the form of commercially available deflectors from various sources, such as Olympus, for example. The X and Y deflectors 41 and 42 are controlled in well known manners and essentially provide the scanning means to scan the beam of light across the tissue sample 50 in the X and Y directions, e.g., select individual portions of the tissue sample 50, one at a time. Lenses 43, 44, 46, 47 and 48 direct source 10 emissions to and receive light from a spot on or in the tissue sample 50 (e.g., a portion of the tissue). Collimating and focusing lenses are also well known. This spot may be moved in the X-Y direction by the scanning means of the X and Y deflectors. Such X-Y confocal scanners are generally known, and one for example can utilize a MEMS device for the X and/or Y deflector.

Where a serial array of 15 gratings spaced by 17.4 meters is incorporated into wavelength slicer and detector 37, a spectrum may be generated in about 2.5 microseconds—as compared to around 0.75 milliseconds for an acousto-optic tunable filter (AOTF) approach.

According to the principles of the present invention, signals returned from sample 50 via scanner 33 may take the form of reflected laser light or may be broadband fluorescence, for example (other applicable optical signals include Raman and two-photon spectroscopies). Confocal scanner 33, as shown in FIG. 2A, may operate with a 1.4 KHz scanning rate over a 300×300 element field, dwelling on each pixel for 2.5 microseconds, such that it takes around 42 milliseconds to scan 300 lines (24 datacubes per second). It may take around 90 milliseconds to do this using an AOTF, even assuming strong light levels and minimal integration times.

According to an embodiment of the present invention, the operation time for the confocal device shown in FIG. 1 can be further reduced (by about a factor of ten) if the signal to noise ratio is sufficient. Further, the structure shown in FIG. 1 is more cost effective and clinically friendly than other systems.

Figure 2B:
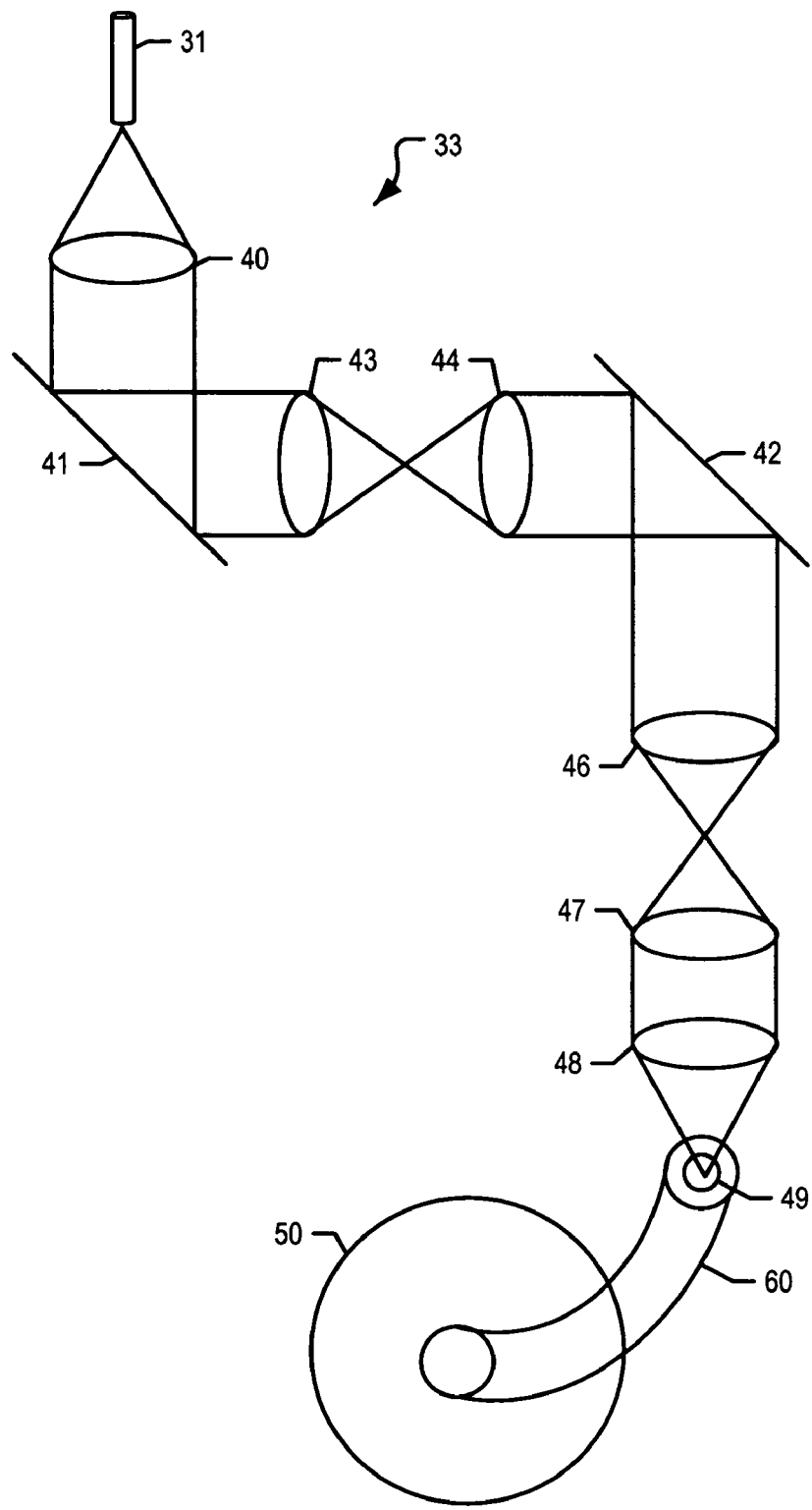
FIG. 2B depicts a scanner configuration suitable for use with in-vivo tissues.

Referring now also to FIG. 2B, there is shown a schematic representation of a confocal scanner well suited for scanning in-vivo tissue samples 50 (one of which is shown), according to an embodiment of the present invention. Like elements in FIGS. 2A and 2B have been labeled using like references. FIG. 2B shows substantially the same structure as depicted in FIG. 2A, with the exception that lens 48 directs light onto and receives light from the face of a fiber optic bundle 49. The fiber optic bundle 49 may be embodied in an endoscope 60, which can be inserted as an imaging fiber bundle into a body cavity or other aperture to perform endoscopy. Thus, as seen in FIG. 2B, confocal scanner 33 scans one end of an imaging fiber bundle 49 endoscope 60. When a specific fiber within bundle 49 is excited by this scanning, the back propagating signal may be collected from the same fiber, thus preserving the imaging properties of bundle 49. Such an endoscope bundle 60 is commercially available from many companies, such as Mauna-Kea Technologies (maunakeatech.com). One such commercially available design has a 600×500 micron field, with a spatial resolution of 5 microns.

Figure 3:
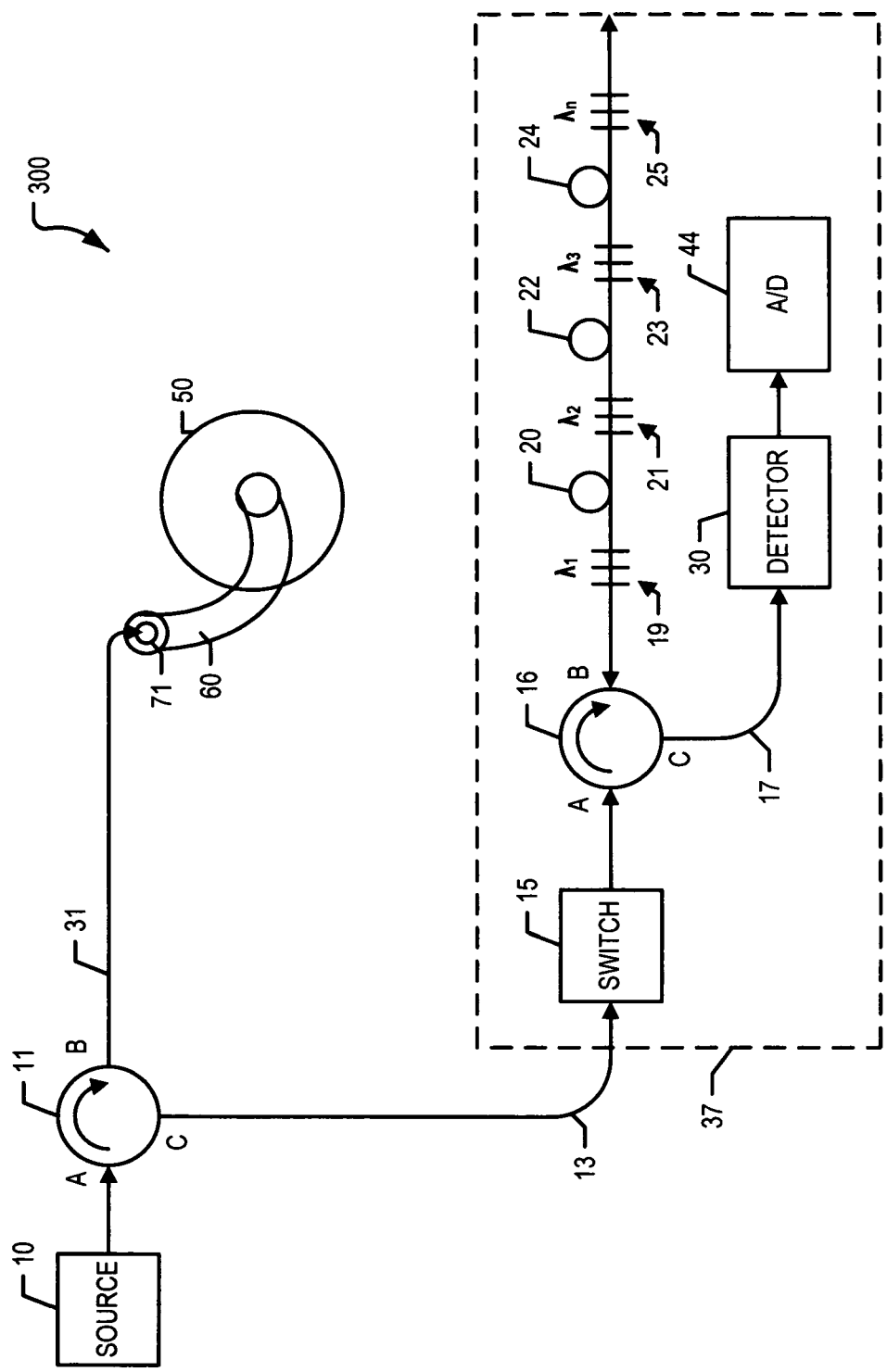
FIG. 3 depicts a fast fiber grating spectrometer employed with another endoscope containing a MEMS scanner.

Referring now to FIG. 3, there is shown a diagram depicting a confocal scanning system 300 according to another embodiment of the invention. Like elements in FIGS. 1 and 3 have been labeled using like references. System 300 may be particularly well suited for scanning in-vivo tissue samples. Like FIG. 1, the embodiment of FIG. 3 illustrates switch 15 as part of spectrometer 37 in an exemplary configuration. However, other configurations are contemplated. For example, it is understood that switch 15 can alternatively be disposed between source 10 and circulator 11. In FIG. 3, port B of circulator 11 is connected directly to a MEMS based confocal scanning head 71 located at the emerged end of an endoscope 60. Such a device including the endoscope 60 may contain two MEMS-based scanners. A MEMS-based scanner is well known in the prior art and need not be described further.

Figure 4:
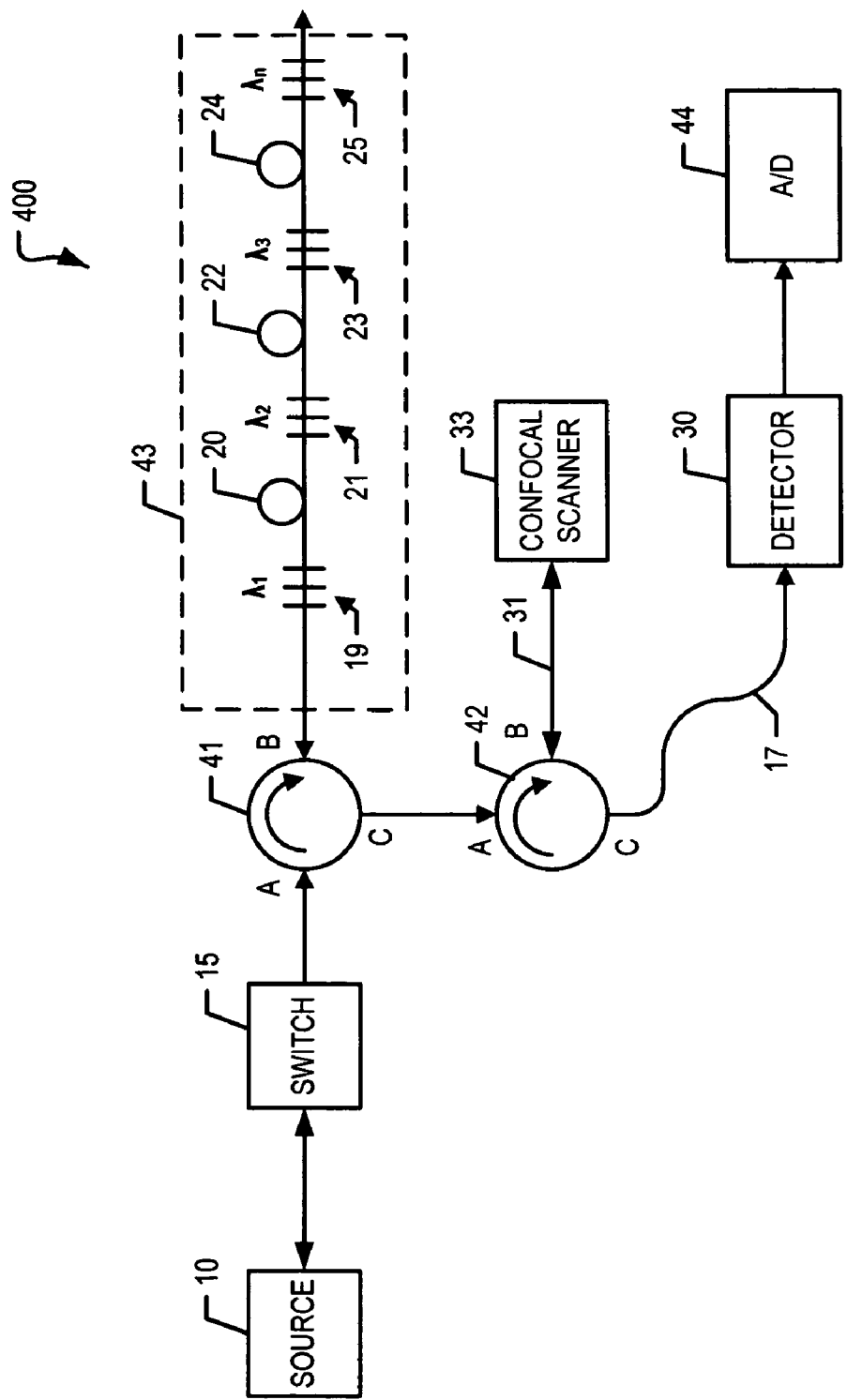
FIG. 4 a fast grating spectrometer utilized with a confocal scanner to scan tissues, according to another embodiment of the invention; and, FIGS. 5 and 6 depict flow diagrams of methods according to embodiments of the present invention.

Referring now to FIG. 4, there is shown a diagram depicting a confocal scanning system 400 according to another embodiment of the invention. Like elements in FIGS. 1 and 4 have been labeled using like references.

System 400 may be particularly well suited for scanning in-vivo and ex-vivo tissue samples.

In the embodiment of system 400, source 10 provides spectrally broad emissions. In general, with regard to the embodiment illustrated in FIG. 4, a broad band signal may be used to measure reflectance of a tissue sample (rather than flourescence). A spectrally broad light signal (obtained via switch 15) is provided directly to the first circulator 41 and into array 43. The serial array of gratings maps the different colors into different time slots so that the spectra that (e.g. red, green and blue) is now returning to the circulator is at staggered time offsets (e.g. blue is coming back to the first circulator before the green and before the red). The time offset spectra frequencies then get routed to the second circulator 42 to the tissue same (not shown) via the confocal scanner, returned and routed to the detector 30 such that the detector detects the reflectance from first the blue, then red, then green signals.

More particularly, emissions emanating from source 10 are applied to the input of switch 15. Switch 15 may again take the form of an optical switch and convert emissions received into a pulse of a given temporal period (i.e., pulse width) at an output thereof. Pulsed source 10 emissions output from switch 15 are applied to the first port A of circulator 41, such as via optical fiber. Circulator 41 operates in a conventional manner to provide sequential outputs, e.g., to couple port A to port B, port B to port C. Port B of circulator 41 is coupled via optical fiber grating and delay array 43, which is akin to the array depicted in and described in conjunction with FIG. 1. In such an embodiment, reflections from array 43 take the form of a temporal sequence of wavelength selective pulses, e.g., a pulse of wavelength $\lambda_1$, followed by a pulse having a wavelength $\lambda_2$, then $\lambda_3$ and so on, until $\lambda_n$. This sequential optical pulse train is directed by circulator 41 to port C.

Port C of circulator 41 is coupled, such as via an optical fiber, to a port A of a circulator 42. Circulator 42 operates in a conventional manner to provide sequential outputs, e.g., to couple port A to port B, port B to port C. Port B of circulator 42 is coupled via optical fiber 31 to confocal scanner 33. Port C of circulator 42 is coupled via optical fiber 17 to detector 30. Confocal scanner 33 may be akin to that described in connection with FIGS. 2A and 2B. Detector 30 may be akin to that described in connection with FIG. 1. Consistently, the sequential optical pulse train input to port A of circulator 42 is directed to confocal scanner 33. Back-emissions therefrom, such as reflections thereof and optical emissions induced thereby, are directed by circulator 42 to port C—and hence to detector 30. Thus, in the embodiment of system 400, detector 30 receives and detects back-emissions to a sequential train of optical pulses having wavelengths that correspond to gratings 19, 21, 23 and 25. Detector 30 may be synchronized with delays 20, 22, 24 to separately detect back-emissions to each of these different wavelengths.

One or more of the configurations described herein may provide several advantages over conventional approaches to tissue examination. One advantage is that the wavelength bin centers and widths can be arranged in an arbitrary manner without regard to the constraints provided by the diffraction equation. Wavelengths from at least around 400 to around 1600 nanometers and full wave, half maximum (FWHM) widths from 1 to 10 nanometers are obtainable.

Also, the wavelength separation method has no influence on spatial scanning fidelity. For example, a map of a given color will spatially register with a map of another color. In this manner, no further constraints are provided in registering different color maps. It should be understood that this neglects chromatic aberration in the scanning optics, which can be compensated for as is known in the art, though.

Further, each polarization state is treated in a similar manner by the optical design. The design is totally compatible with the confocal optics as shown in the figures. In each figure, the fiber aperture where the optical fiber 31 connects to free space optics serves as the confocal pinhole. For example in FIG. 1 the OSA is connected to the confocal scanning head which scans an ex-vivo tissue or other sample.

Further, the configurations of the present invention, for example that of FIG. 1 is useful in combination with both confocal microscopes designed for millimeter fields and confocal macroscopes designed for centimeter (cm) fields, such as that described in U.S. Pat. No. 5,737,121, the entire disclosure of which is hereby incorporated by reference herein. Further yet, the designs are compatible with broad band light sources, such as those used for reflectance studies and with laser sources used for inducing fluorescence, 2-photon, and Raman spectra.

Where detector 30 takes the form of a single element, it operates at a rate faster than detector arrays conventionally used in the AOTF method (preferably about 500 times faster). Useful signal to noise ratios in the visible range can be obtained with photomultiplier tubes. Silicon detectors can also be useful at wavelengths below one micron, while InGaAs based PINS and avalanche photo diodes can be employed for longer wavelengths. InGaAs detectors with thin InP cap layers can operate across the visible and the near infrared bands.

The output of the detector may be applied to an analog to digital converter (A/D), such as is shown in FIG. 4 and designated 44. Such converters are well known, and may digitize the detector 30 signal with 14 bit resolution at 175 million samples per second, for example. To operate with single photon counting, excitation source 10 may need to be isolated from wavelength slicer and detector 37, and counts may be summed over many scans. In this manner, colors in a scanned map can grow over multiple acquisitions similar to photon-starved astronomical observations.

In certain embodiments of the present invention, a Nikon model C1si, Olympus model FluoView 300, or Mauna Kea Technologies model Celivizio confocal scanners may be used. In certain embodiments of the present invention, one or more Hamamatsu model H9656-20MOD photo multipliers may be used. In certain embodiments of the present invention, bragg grating arrays that are commercially available through OFS Fitel Specialty Fiber Products, Teraxion, Avensys and/or OE Land may be used.

Figure 5:
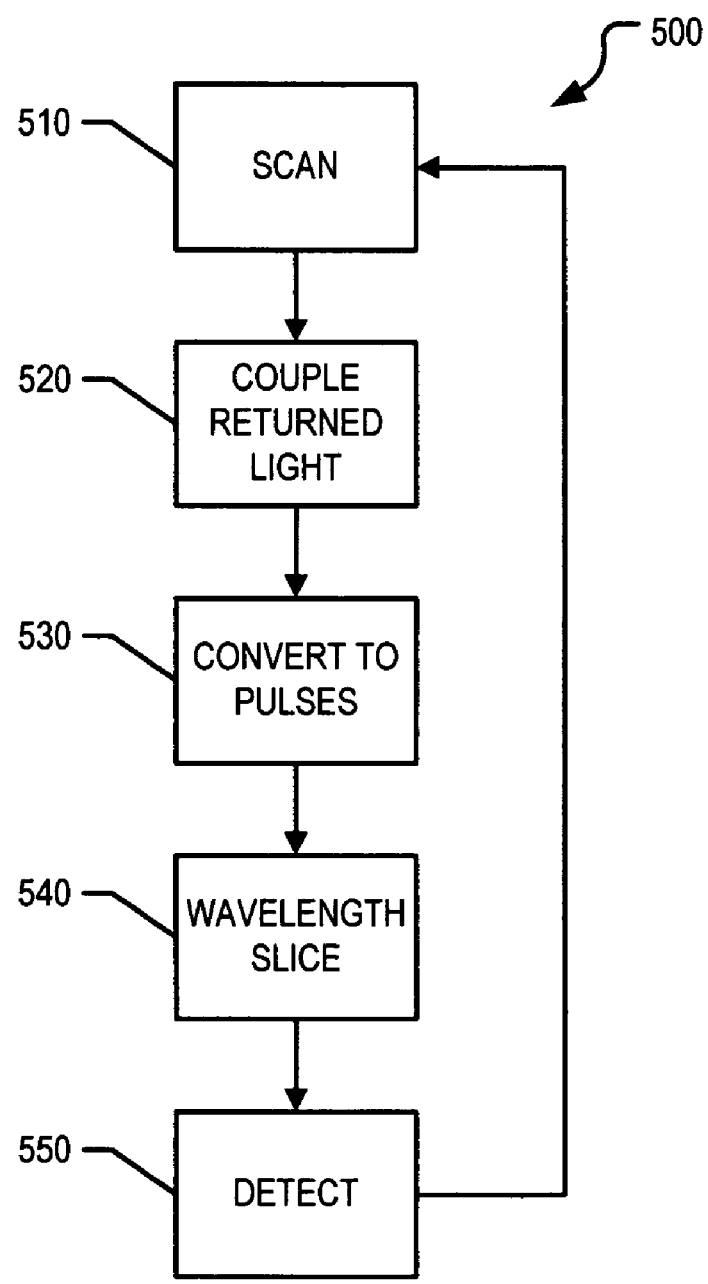

Referring now to FIG. 5, there is shown a flow diagram of a method 500 according to an embodiment of the present invention. Method 500 of FIG. 5 may be particularly well suited for use with the apparatus of FIGS. 1 and 3, for example. Method 500 will be discussed as it relates to the apparatus of FIGS. 1 and 2, for non-limiting purposes of explanation only.

Method 500 commences with scanning a portion of a subject tissue at block 510. The tissue may be in-vivo or ex-vivo. The scanning may include illuminating a selected portion of the tissue using source 10, through circulator 11 and optical fiber 31, using confocal scanner 33. The portion of the tissue may be selected by positioning deflectors 41, 42 (FIG. 2) in a predetermined or corresponding manner, for example.

At block 520, intensity signals from the then scanned portion of the tissue are coupled into an end of optical fiber 31, which provides a confocal pinhole. At block 530, the intensity signals are converted to optical pulses, such as by switch or modulator 15. It is understood, however, that block 530 can be either as shown or placed before block 510.

At block 540, a temporal sequence of wavelength selective reflections of the optical pulses is provided, such as by gratings 19, 21, 23, 25 and delay elements 20, 22, 24. At block 550, an output indicative of a relative intensity responsively to the temporal sequence of wavelength selective reflections is provided, such as by detector 30.

Thereafter, another portion of the tissue may be scanned, such that processing returns to block 510.

Figure 6:
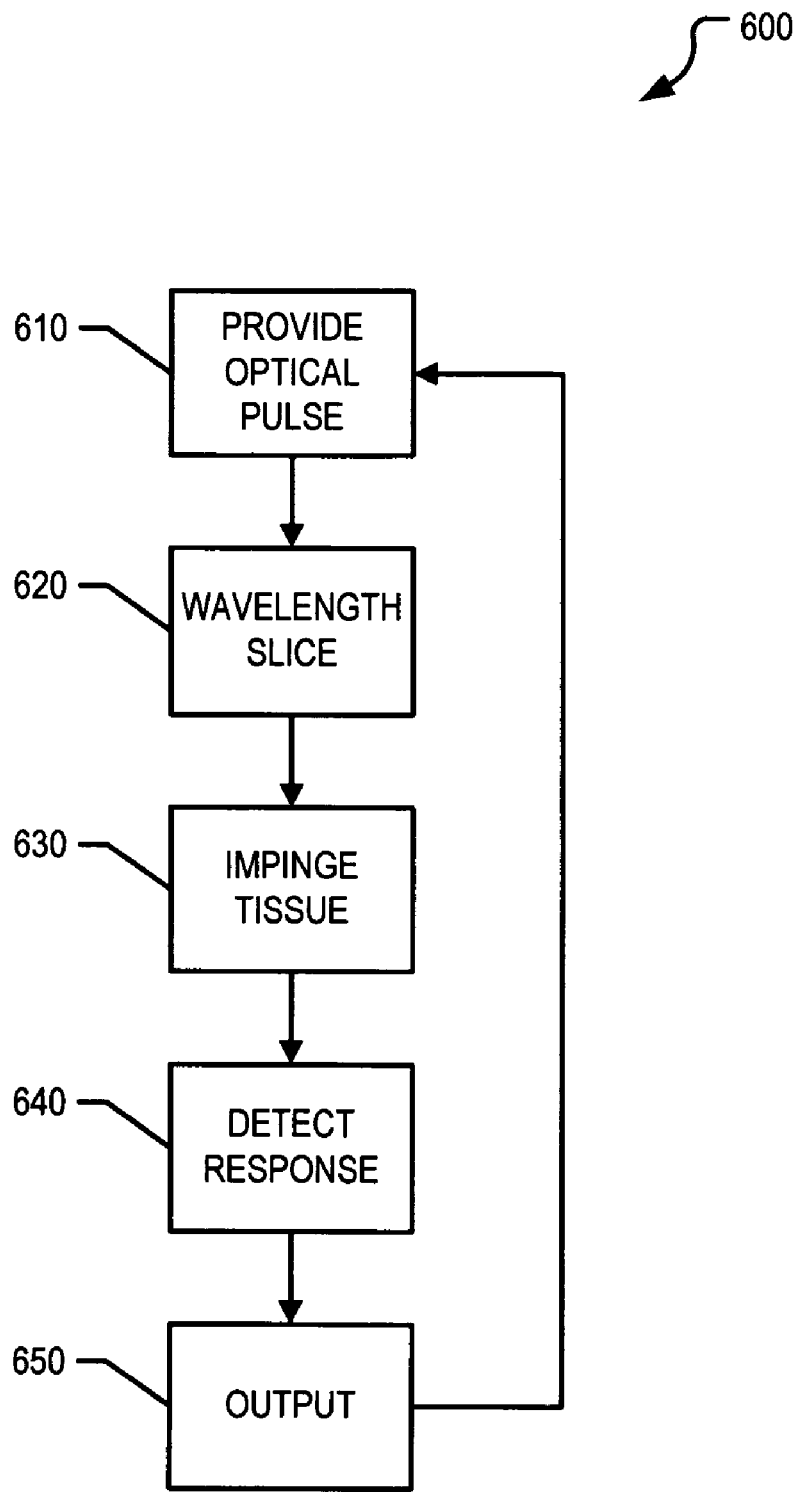

Referring now to FIG. 6, there is shown a flow diagram of a method 600 according to another embodiment of the present invention. Method 600 of FIG. 6 may be particularly well suited for use with the apparatus of FIG. 4, for example. Method 600 will be discussed as it relates to the apparatus of FIGS. 4 and 2, for non-limiting purposes of explanation only.

Method 600 commences with providing a temporal series of optical pulses at block 610 (one pulse is generated each time processing returns to block 610). This may be accomplished using source 10 and switch 15, for example. Alternatively, source 10 may be directly modulated to provide the temporal series of optical pulses, such that switch 15 may be omitted. At block 620, a temporal sequence of wavelength selective reflections of each of the optical pulses is provided, such as by using gratings 19, 21, 23, 25 and delay elements 20, 22, 24. At block 630, a tissue portion corresponding to the then provided pulse is impinged with the temporal sequence of wavelength selective reflections of the corresponding pulse. This may be accomplished using confocal scanner 33, for example. At block 640, light returned from each portion of the plurality responsively to the impinging is detected, such as by using detector 30. And, at block 650 an output indicative of a relative intensity for each portion of the tissue responsively to the detecting is provided, such as to or by A/D 44.

It will be apparent to those skilled in the art that modifications and variations may be made in the apparatus and process of the present invention without departing from the spirit or scope of the invention. It is intended that the present invention cover the modification and variations of this invention provided they come within the scope of the appended claims and their equivalents.

What is claimed is:

1. A system for multispectral confocal mapping of a tissue, comprising:
   a light source providing emissions;
   an optical fiber having a first end optically coupled to receive the emissions and a second end having an aperture providing a confocal pinhole,
   a scanner being free-space coupled to said aperture, said scanner operative to scan the tissue and provide intensity signals for each of a plurality of points therein, wherein said optical fiber receives the intensity signals at said aperture and propagates said intensity signals to said first end;
   a switch or modulator optically coupled to said first end of said optical fiber and operative to convert said intensity signals to optical pulses;
   a reflector optically coupled to receive the optical pulses and provide a temporal sequence of wavelength selective reflections of the optical pulses; and,
   a detector optically coupled to receive the temporal sequence of wavelength selective reflections and provide an output suitable for populating a data cube indicative of the relative intensity of each point in the scanned tissue.

2. The system of claim 1, wherein the optical fiber is a single mode fiber.

3. The system of claim 1, wherein the optical fiber is a multi-mode fiber.

4. The system of claim 1, wherein the optical fiber is a microstructured fiber.

5. The system of claim 1, wherein the optical fiber is a polarization maintaining fiber.

6. The system of claim 1, wherein said optical fiber has a diameter between about 1 and 3 microns for visible wavelengths.

7. The system of claim 1, wherein said optical fiber has a diameter greater than about 3 microns for visible wavelengths.

8. The system of claim 1, wherein the reflector comprises a series coupled array of fiber gratings.

9. The system of claim 8, wherein the array of fiber gratings is unblazed.

10. The system of claim 8, wherein said array comprises at least about 10 gratings.

11. The system of claim 8, wherein said array comprises between about 20 and 50 gratings.

12. The system of claim 8, wherein said array comprises between about 10 and 100 gratings.

13. The system of claim 1, wherein the tissue comprises an ex-vivo tissue sample.

14. The system of claim 1, wherein the tissue comprises an in-vivo tissue sample.

15. The system of claim 14, wherein the scanner comprises an endoscope fiber bundle.

16. The system of claim 1, wherein said scanner comprises an x-y MEMS scanner at least partially contained in an endoscope.

17. The system of claim 1, wherein each optical pulse has a pulse width less than a delay between successive wavelength selective reflections in the temporal sequence of wavelength selective reflections.

18. The system of claim 1, wherein the scanner is a resonant scanner.

19. The system of claim 1, wherein said detector comprises a PIN detector.

20. The system of claim 1, wherein said detector comprises a photomultiplier tube.

21. The system of claim 1, wherein said detector comprises avalanche photodetector.

22. The system of claim 1, wherein said wavelength selective reflections have wavelengths between about 400 and 1600 nanometers.

23. The system of claim 1, wherein said reflector comprises a single chirped grating.

24. The system of claim 1, wherein said scanner operates on millimeter (mm) scale fields.

25. The system of claim 1, wherein the scanner operates on centimeter (cm) scale fields.

26. The system of claim 1, wherein said light source comprises a laser.

27. The system of claim 1, wherein said light source comprises one or more narrow band sources.

28. The system of claim 1, wherein said light source comprises a broad band light source.

29. The system of claim 1, wherein said optical fiber has a diameter between about 8-10 microns for the near infrared region.

30. A system for multispectral confocal mapping of a tissue, comprising:
- a light source providing a series of broad spectrum emission pulses;
- a plurality of reflectors optically coupled to receive the series of optical pulses and provide a temporal sequence of wavelength selective reflections of each of the optical pulses;
- an optical fiber having a first end optically coupled to receive the temporal sequence of wavelength selective reflections and a second end having an aperture providing a confocal pinhole,
- a scanner being free-space coupled to said aperture, said scanner operative to scan the tissue and provide intensity signals for each of a plurality of points therein, wherein said optical fiber receives the intensity signals at said aperture and propagates said intensity signals to said first end; and,
- a detector optically coupled to receive the intensity signals and provide an output suitable for populating a data cube indicative of the relative intensity of each point in the scanned tissue.

31. A method for mapping a tissue, comprising:
scanning portions of the tissue, and for each portion:
- coupling intensity signals from the then scanned portion of the tissue into an end of an optical fiber providing a confocal pinhole;
- converting said intensity signals to optical pulses;
- obtaining a temporal sequence of wavelength selective reflections of the optical pulses; and,
- providing an output indicative of a relative intensity responsively to the temporal sequence of wavelength selective reflections.

32. A method for mapping tissue, comprising:
- providing a temporal series of optical pulses;
- providing a temporal sequence of wavelength selective reflections of each of the optical pulses;
- impinging portions of the tissue with a corresponding one of the temporal sequence of wavelength selective reflections;
- detecting light returned from each portion responsive to the impinging step; and
- providing, in response to said detecting step, an output indicative of a relative intensity for each said portion of the tissue.

* * * * *